United States Patent [19]

McRae

[11] Patent Number: Plant 6,502

[45] Date of Patent: Jan. 3, 1989

[54] LILY PLANT NAMED GISELLE

[75] Inventor: Edward A. McRae, Boring, Oreg.

[73] Assignee: Melridge, Inc., Gresham, Oreg.

[21] Appl. No.: 27,622

[22] Filed: Mar. 18, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new variety of lily plant bearing outfacing to semi-upright flowers particularly characterized by their pure white coloration, their exceptionally large size and their tepals having frilled and fluted margins. These characteristics, together with their outfacing to semi-upright orientation, provide a combination that is completely new in the Oriental hybrid divisions of lilies suited to forcing and to mass commercial cultivation. The plant is highly resistant to disease and shows tolerance of virus, is an excellent garden plant, and the bulbs may be precooled and forced for cut flower production.

1 Drawing Sheet

BACKGROUND OF THE INVENTION

This new variety of lily plant originated as a seedling which first flowered at Sandy, Oreg., in 1977 and is one of a group of seedlings planted by me with the object of producing large flowered, semi-upright Oriental hybrids with increased virus tolerance and suited to forcing into flower out-of-season, heretofore unknown in the lily breeding art.

The desired objective was achieved by my using as the mother plant a selected seedling from the 'Imperial Silver' strain and a selected form of the species *Lilium nobilissimum* as the pollen parent. The selected seedling resulting from this parentage produces flowers having an outfacing, semi-upright orientation, extremely large in size with unusually broad tepals which have distinctly frilled and fluted margins, unusually thick substance and pure white coloration, a combination unique among Oriental hybrid lilies; and it also possesses unusually strong, stout stems with exceptionally broad leaves. It was for these reasons that this seedling was selected by me for propagation, and I asexually reproduced the plant at Sandy, Oreg. by bulb scale propagation and also by natural propagation from bulblets with such success that propagation was carried on through several successive generations by bulb scale propagation and by tissue culturing from bulb scale explants. It was thereby determined that the novel and distinctive characteristics of the new variety would hold true under asexual propagation from generation to generation and appeared to be firmly fixed.

The clone of this new variety was found to be vigorous and a good grower and propagator, as observed at Sandy, Oreg., and it was also found to be well suited to forcing out-of-season when the bulbs are dug at the appropriate time and properly precooled. For example, late October-dug bulbs, properly precooled and potted in January, will flower under glass in western Oregon, in an average of one hundred and ten to one hundred and fifteen days, with no supplementary lighting and at moderate greenhouse temperatures.

DESCRIPTION OF THE DRAWING

My new variety of lily plant is illustrated by the accompanying photographic drawing, which shows a fully opened bloom and some foliage in full color and illustrates the flower form, the tepal arrangement, and in particular, the novel and distinctive flower size, form, outfacing orientation and the pure white, unspotted flowers with their broad tepals with fluted margins.

DESCRIPTION OF THE NEW VARIETY

The following is a detailed description of my new variety of Asiatic hybrid lily, with nomenclature according to The International Lily Register (The Royal Horticultural Society of London, England, 2nd edition, 1969), and with color designations according to The R.H.S. Colour Chart published by The Royal Horticultural Society in 1966.

THE PLANT

Origin: Seedling.

Parentage:

- *Seed parent.*—A selected clone from the 'Imperial Silver' strain (an unnamed and unpatented variety).
- *Pollen parent.*—A selected clone of *Lilium nobilissimum* (unpatented).

Classification:

- *Horticultural.*—Division VII-B, bowl-shaped Oriental hybrid lily, according to The Horticultural Classification of Lilies by The Royal Horticultural Society of London, England.
- *Commercial.*—Hybrid Lilium Clone.

Form: Single stem, upright and stately.

Height: About 70 to 125 cm. from bulbs having a circumference of about 14 to 18 cm., provided that the light levels are adequate. Low light levels may cause "Stretching".

Growth: Vigorous and upright.

Foliage:

- *Quantity.*—Abundant.
- Leaf size.—About 8 to 10 cm. wide and about 12 to 15 cm. long.
- *Leaf shape.*—Generally elliptical to linear with acuminate tip.
- *Texture.*—Leathery.
- *Aspect.*—Glossy.
- *Color.*—Medium green, but lighter on the under side.

Bulbs:

*Size.*—Various and ranging up to 25 cm. In circumference in commercial use.

*Color.*—White, with flushes of soft pink or soft yellow after exposure to light.

THE BUD

Form: Long ovoid with rounded base and obtuse tip.

Size: About 12 to 20 cm. long and about 12 to 16 cm. in circumference just prior to opening.

Opening rate: The bud opens slowly, taking about one hour in response to morning light.

Color: Whitish with soft green midribs.

Peduncle:

*Length.*—Averages about 4 to 6 cm., but may elongate to a greater extent if the light levels are too low or if the bulbs have been improperly stored prior to forcing.

*Color.*—Medium green with a very light plum overlay.

THE FLOWER

Blooming habit. Once annually and profusely in midseason.

Size: Exceptionally large, averaging 25 to 30 cm. in diameter, reflexing at the tepal tips on the second day to a spread of about 20 to 25 cm. in diameter.

Borne: As a raceme inflorescence having three to eight flowers from a bulb of about 14 to 18 cm. in circumference.

Shape: As a broad bowl by the second day, with the "bowl" about 10 cm. deep.

Tepalage: Typical of genus Lilium with six imbricated tepals having fluted margins.

*Size.*—Outer tepals — About 4 to 5 cm. wide. Inner tepals — About 6 to 8 cm. wide.

Color: The flowers are distinguished by their pure white coloration. The nectary furrows are apple green.

Aspect: Shiny.

Spotting: The tepals are unspotted.

Longevity: The tepals stay on the stems about three weeks.

Pedicel:

*Length.*—In average, about 8 to 12 cm.

*Form.*—Sturdy and ascending up to about 45 degrees from the horizontal.

Flower fragrance: Distinct and pleasing.

Lasting quality: The flower is long lasting, both on the plant and as a cut flower.

Disease resistance: The flower and plant are resistant to disease; and in particular, they are resistant to Fusarium bulb rot and Botrytis blight, as observed in western Oregon.

REPRODUCTIVE ORGANS

Stamens:

*Number.*—Six.

*Arrangement.*—Typical of the genus Lilium.

*Anthers (dehisced) and pollen.*—Color: Grayed red, 170A, in the new flower fading in bright sunlight to 167A.

*Filaments.*—Length: About 5 to 10 cm. Color: Soft green to white.

Pistil:

*Number.*—One.

*Style.*—About 8 to 10 cm. long.

*Stigma.*—Size: Very large. Color: Color: Soft greenish white.

Ovary: Characteristic of the genus Lilium.

THE FRUIT

Fertility: The fruit is fertile.

Shape: Ovoid.

Color at maturity: Soft brown, sometimes overlaid with soft plum.

This new variety of Oriental hybrid lily most nearly resembles *Lilium nobilissimum,* but is taller with stronger stems, and its flowers are conspicuously larger. The flowers of the new variety are side facing to semi-upright rather than completely upfacing as those of *Lilium nobilissimum* and its flower form is more bowl-shaped and less trumpet-formed. This new plant also resembles the related variety 'Swan-Song', but it can be distinguished by its much larger flower, broader tepals, broader leaves, lighter pollen color, lighter stigma color, and more descending leaves.

I claim:

1. The new and distinctive variety of Oriental hybrid lily plant and parts thereof, substantially as herein shown and described, characterized by its unique side facing to semi-upright orientation, and its pure white flowers of exceptionally large size; its high resistance to diseases, its vigorous growth habit, and excellence of its flower form and substance.

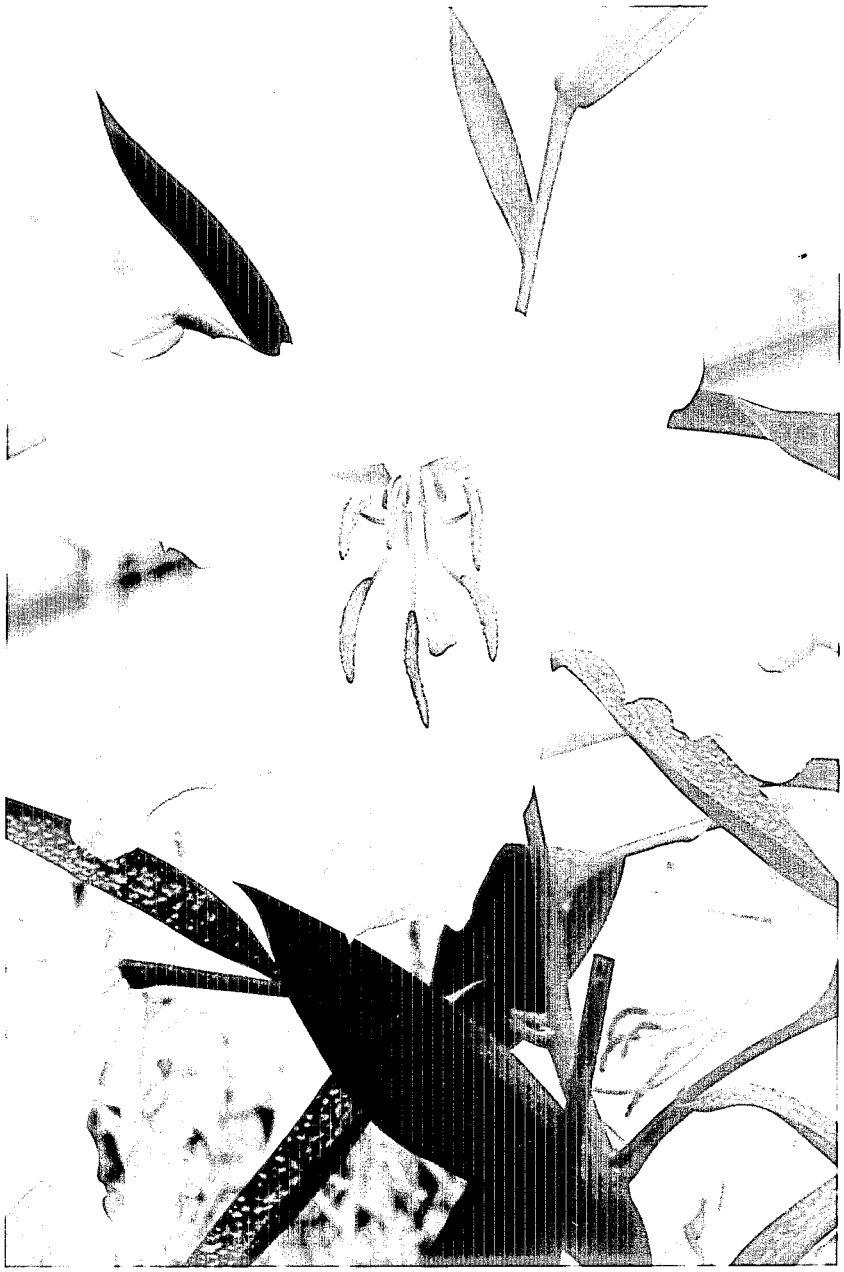

* * * * *